United States Patent
Le et al.

(10) Patent No.: US 8,111,402 B2
(45) Date of Patent: Feb. 7, 2012

(54) OPTICAL SENSING BASED ON OVERLAPPING OPTICAL MODES IN OPTICAL RESONATOR SENSORS AND INTERFEROMETRIC SENSORS

(75) Inventors: Thanh M. Le, Duarte, CA (US); Nan Yu, Arcadia, CA (US); Lutfollah Maleki, Pasadena, CA (US); Anatoliy Savchenkov, Glendale, CA (US); William H. Steier, San Marino, CA (US)

(73) Assignees: OEwaves, Inc., Pasadena, CA (US); California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 319 days.

(21) Appl. No.: 12/418,525

(22) Filed: Apr. 3, 2009

(65) Prior Publication Data
US 2009/0251705 A1    Oct. 8, 2009

Related U.S. Application Data

(60) Provisional application No. 61/072,894, filed on Apr. 3, 2008.

(51) Int. Cl.
*G01B 9/02* (2006.01)
(52) U.S. Cl. ........................................ 356/491; 356/480
(58) Field of Classification Search .................. 356/461, 356/460, 459, 480, 481, 491, 517, 437, 432
See application file for complete search history.

(56) References Cited

U.S. PATENT DOCUMENTS

| | | |
|---|---|---|
| 5,204,640 A | 4/1993 | Logan, Jr. |
| 5,220,292 A | 6/1993 | Bianchini et al. |
| 5,723,856 A | 3/1998 | Yao et al. |
| 5,751,747 A | 5/1998 | Lutes et al. |
| 5,777,778 A | 7/1998 | Yao |
| 5,917,179 A | 6/1999 | Yao |
| 5,929,430 A | 7/1999 | Yao et al. |
| 5,985,166 A | 11/1999 | Unger et al. |
| 6,080,586 A | 6/2000 | Baldeschwieler et al. |
| 6,178,036 B1 | 1/2001 | Yao |
| 6,203,660 B1 | 3/2001 | Unger et al. |
| 6,389,197 B1 | 5/2002 | Iltchenko et al. |
| 6,417,957 B1 | 7/2002 | Yao |

(Continued)

FOREIGN PATENT DOCUMENTS
WO    01/96936    12/2001
(Continued)

OTHER PUBLICATIONS

Armani, A., et al., "Label-Free, Single-Molecule Detection with Optical Microcavities," *Science*, 317(5839):783-787, Aug. 2007.

(Continued)

*Primary Examiner* — Hwa Lee
(74) *Attorney, Agent, or Firm* — Perkins Coie LLP

(57) ABSTRACT

Techniques and devices based on transverse magnetic (TM) and transverse electric (TE) modes in an optical resonator or interferometer to provide sensitive optical detection with insensitivity to a change in temperature. A shift in a difference between a first resonance wavelength of a TE optical mode and a second resonance wavelength of a TM optical mode is measured to measure a change in a sample that is in optical interaction with the optical resonator or interferometer. For example, the detected shift can be used to measure a change in a refractive index of the sample.

30 Claims, 10 Drawing Sheets

U.S. PATENT DOCUMENTS

| | | | |
|---|---|---|---|
| 6,473,218 B1 | 10/2002 | Maleki et al. | |
| 6,476,959 B2 | 11/2002 | Yao | |
| 6,487,233 B2 | 11/2002 | Maleki et al. | |
| 6,488,861 B2 | 12/2002 | Iltchenko et al. | |
| 6,490,039 B2 | 12/2002 | Maleki et al. | |
| 6,535,328 B2 | 3/2003 | Yao | |
| 6,567,436 B1 | 5/2003 | Yao et al. | |
| 6,580,532 B1 | 6/2003 | Yao et al. | |
| 6,594,061 B2 | 7/2003 | Huang et al. | |
| 6,762,869 B2 | 7/2004 | Maleki et al. | |
| 6,781,696 B1 * | 8/2004 | Rosenberger et al. | 356/437 |
| 6,795,481 B2 | 9/2004 | Maleki et al. | |
| 6,798,947 B2 | 9/2004 | Iltchenko | |
| 6,853,479 B1 | 2/2005 | Ilchenko et al. | |
| 6,871,025 B2 | 3/2005 | Maleki et al. | |
| 6,873,631 B2 | 3/2005 | Yao et al. | |
| 6,879,752 B1 | 4/2005 | Ilchenko et al. | |
| 6,901,189 B1 | 5/2005 | Savchenkov et al. | |
| 6,906,309 B2 | 6/2005 | Sayyah et al. | |
| 6,922,497 B1 | 7/2005 | Savchenkov et al. | |
| 6,928,091 B1 | 8/2005 | Maleki et al. | |
| 6,943,934 B1 | 9/2005 | Ilchenko et al. | |
| 6,987,914 B2 | 1/2006 | Savchenkov et al. | |
| 7,024,069 B2 | 4/2006 | Savchenkov et al. | |
| 7,043,117 B2 | 5/2006 | Matsko et al. | |
| 7,050,212 B2 | 5/2006 | Matsko et al. | |
| 7,061,335 B2 | 6/2006 | Maleki et al. | |
| 7,062,131 B2 | 6/2006 | Ilchenko | |
| 7,092,591 B2 | 8/2006 | Savchenkov et al. | |
| 7,133,180 B2 | 11/2006 | Ilchenko et al. | |
| 7,173,749 B2 | 2/2007 | Maleki et al. | |
| 7,184,451 B2 | 2/2007 | Ilchenko et al. | |
| 7,187,870 B2 | 3/2007 | Ilchenko et al. | |
| 7,218,662 B1 | 5/2007 | Ilchenko et al. | |
| 7,248,763 B1 | 7/2007 | Kossakovski et al. | |
| 7,260,279 B2 | 8/2007 | Gunn et al. | |
| 7,283,707 B1 | 10/2007 | Maleki et al. | |
| 7,369,722 B2 | 5/2008 | Yilmaz et al. | |
| 7,389,053 B1 | 6/2008 | Ilchenko et al. | |
| 7,400,796 B1 | 7/2008 | Kossakovski et al. | |
| 7,440,651 B1 | 10/2008 | Savchenkov et al. | |
| 7,460,746 B2 | 12/2008 | Maleki et al. | |
| 7,801,189 B2 * | 9/2010 | Maleki et al. | 372/26 |
| 2001/0038651 A1 | 11/2001 | Maleki et al. | |
| 2002/0018611 A1 | 2/2002 | Maleki et al. | |
| 2002/0018617 A1 | 2/2002 | Iltchenko et al. | |
| 2002/0021765 A1 | 2/2002 | Maleki et al. | |
| 2002/0080842 A1 | 6/2002 | An et al. | |
| 2002/0081055 A1 | 6/2002 | Painter et al. | |
| 2002/0085266 A1 | 7/2002 | Yao | |
| 2002/0097401 A1 | 7/2002 | Maleki et al. | |
| 2003/0160148 A1 | 8/2003 | Yao et al. | |
| 2004/0100675 A1 | 5/2004 | Matsko et al. | |
| 2004/0109217 A1 | 6/2004 | Maleki et al. | |
| 2004/0218880 A1 | 11/2004 | Matsko et al. | |
| 2004/0240781 A1 | 12/2004 | Savchenkov et al. | |
| 2005/0017816 A1 | 1/2005 | Ilchenko et al. | |
| 2005/0063034 A1 | 3/2005 | Maleki et al. | |
| 2005/0074200 A1 | 4/2005 | Savchenkov et al. | |
| 2005/0123306 A1 | 6/2005 | Ilchenko et al. | |
| 2005/0128566 A1 | 6/2005 | Savchenkov et al. | |
| 2005/0175358 A1 | 8/2005 | Ilchenko et al. | |
| 2005/0248823 A1 | 11/2005 | Maleki et al. | |
| 2007/0009205 A1 | 1/2007 | Maleki et al. | |
| 2007/0153289 A1 | 7/2007 | Yilmaz et al. | |
| 2008/0001062 A1 | 1/2008 | Gunn et al. | |
| 2008/0075464 A1 | 3/2008 | Maleki et al. | |
| 2008/0310463 A1 | 12/2008 | Maleki et al. | |

FOREIGN PATENT DOCUMENTS

| | | |
|---|---|---|
| WO | 2005/038513 | 4/2005 |
| WO | 2005/055412 | 6/2005 |
| WO | 2005/067690 | 7/2005 |
| WO | 2005/119217 | 12/2005 |
| WO | 2005/122346 | 12/2005 |
| WO | 2006/076585 | 7/2006 |
| WO | 2007/143627 | 12/2007 |

OTHER PUBLICATIONS

Arnold, S., et al., "Shift of whispering-gallery modes in microspheres by protein adsorption," *Optics Letters*, 28(4):272-274, Feb. 2003.

Boyd, R., et al., "Sensitive disk resonator photonic biosensor," *Applied Optics*, 40(31):5742-5747, Nov. 2001.

Braginsky, V.B., et al., "Quality-Factor and Nonlinear Properties of Optical Whispering-Gallery Modes," *Physics Letters A*, 137(7, 8):393-397, May 1989.

Chao, C.-Y., et al., "Polymer Microring Resonators for Biochemical Sensing Applications," *IEEE Journal of Selected Topics in Quantum Electronics*, 12(1):134-142, Jan./Feb. 2006.

Eliyahu, D., et al., "Low Phase Noise and Spurious Levels in Multi-Loop Opto-Electronic Oscillators," *Proceedings of the 2003 IEEE International Frequency Control Sympsoium and PDA Exhibition*, pp. 405-410, May 2003.

Eliyahu, D., et al., "Modulation Response ($S_{21}$) of the Coupled Opto-Electronic Oscillator," *Proceedings of the 2005 IEEE International Frequency Control Symposium and Exposition*, pp. 850-856, Aug. 2005.

Eliyahu, D., et al., "Tunable, Ultra-Low Phase Noise YIG Based Opto-Electronic Oscillator," *IEEE MTT-S International Microwave Symposium Digest*, 3:2185-2187, Jun. 2003.

Gorodetsky, M.L., et al., "Optical Microsphere Resonators: Optimal Coupling to High-$Q$ Whispering-Gallery Modes," *J.Opt. Soc. Am. B*, 16(1):147-154, Jan. 1999.

Gorodetsky, M.L., et al., "Rayleigh Scattering in High-$Q$ Microspheres," *J. Opt. Soc. Am. B*, 17(6):1051-1057, Jun. 2000.

Gorodetsky, M.L., et al., "Ultimate $Q$ of Optical Microsphere Resonators," *Optics Letters*, 21(7):453-455, Apr. 1996.

Hanumegowda, N., et al., "Refractometric sensors based on microsphere resonators," *Applied Physics Letters*, 87(20):201107.1-201107.3, Nov. 2005.

Hryniewicz, J.V., et al., "Higher Order Filter Response in Coupled Microring Resonators," *IEEE Photonics Technology Letters*, 12(3):320-322, Mar. 2000.

Huang, S., et al., "A 'Turnkey' Optoelectronic Oscillator with Low Acceleration Sensitivity," *2000 IEEE/EIA International Frequency Control Symposium and Exhibition*, pp. 269-279, Jun. 2000.

Ilchenko, V., et al., "Electrooptically Tunable Photonic Microresonators and Photonic Bandgap Waveguide Coupling for Micro-Optoelectronic Oscillators," *GOMACTech 2003*, Tampa, Florida, pp. 1-4.

Ilchenko, V., et al., "High-Q Microsphere Cavity for Laser Stabilization and Optoelectronic Microwave Oscillator," *Proceedings SPIE Microresonators and Whispering-Gallery Modes*, vol. 3611, pp. 190-198, Jan. 1999.

Ilchenko, V., et al., "Microsphere Integration in Active and Passive Photonics Devices," *Proc. of SPIE Laser Resonators III*, vol. 3930, pp. 154-162, Jan. 2000.

Ilchenko, V., et al., "Microtorus: A High-Finesse Microcavity with Whispering-Gallery Modes," *Optics Letters*, 26(5):256-258, Mar. 2001.

Ilchenko, V., et al., "Pigtailing the High-$Q$ Microsphere Cavity: A Simple Fiber Coupler for Optical Whispering-Gallery Modes," *Optics Letters*, 24(11):723-725, Jun. 1999.

Ilchenko, V., et al., "Sub-Micro Watt Photonic Microwave Receiver," *IEEE Photonics Technology Letters*, 14(11):1602-1604, Nov. 2002.

Ilchenko, V., et al., "Tunability and Synthetic Lineshapes in High-Q Optical Whispering Gallery Modes," *Proc. of SPIE Laser Resonators and Beam Control VI*, vol. 4969, pp. 195-206, Jan. 2003.

Ilchenko, V., et al., "Whispering-Gallery-Mode Electro-Optic Modulator and Photonic Microwave Receiver," *J. Opt. Soc. Am. B*, 20(2):333-342, Feb. 2003.

Ito, H., et al., "InP/InGaAs Uni-Travelling-Carrier Photodiode with 310 GHz Bandwidth," *Electronics Letters*, 36(21):1809-1810, Oct. 2000.

Ksendzov, A., et al., "Integrated optics ring-resonator sensors for protein detection," *Optics Letters*, 30(24):3344-3346, Dec. 2005.

Le, T., et al., "Optical Resonant Sensors: A Method to Reduce the Effect of Thermal Drift," *Applied Optics*, 48(3):458-463, Feb. 2009.

Logan, R., et al., "Stabilization of Oscillator Phase Using a Fiber-Optic Delay-Line," *IEEE 45th Annual Symposium on Frequency Control*, pp. 508-512, May 1991.

Maleki, L., "The Opto-Electronic Oscillator: Prospects for Extending the State of the Art in Reference Frequency Generation," *International Topical Meeting on Microwave Photonics*, pp. 195-198, Oct. 1998.

Matsko, A., et al., "Active Mode Locking with Whispering-Gallery Modes," *J. Opt. Soc. Am. B*, 20(11):2292-2296, Nov. 2003.

Matsko, A., et al., "Optical Resonators with Whispering-Gallery Modes-Part I: Basics," *IEEE Journal of Selected Topics in Quantum Electronics*, 12(1):3-14, Jan./Feb. 2006.

Matsko, A., et al., "Whispering-Gallery-Mode based Optoelectronic Microwave Oscillator," *Journal of Modern Optics*, 50(15-17):2523-2542, Feb. 2004.

Matsko, A., et al., "Whispering-Gallery-Mode Resonators as Frequency References. I. Fundamental Limitations," *J. Opt. Soc. Am. B*, 24(6):1324-1335, Jun. 2007.

Myers, L.E., et al., "Quasi-Phase-Matched Optical Parametric Oscillators in Bulk Periodically Poled $LiNbO_3$," *J. Opt. Soc. Am. B*, 12(11):2102-2116, Nov. 1995.

Savchenkov, A., et al., "Whispering-Gallery-Mode Resonators as Frequency References. II. Stabilization," *J. Opt. Soc. Am. B*, 24(12):2988-2997, Dec. 2007.

Schmitt, K., et al., "Interferometric biosensor based on planar optical waveguide sensor chips for label-free detection of surface bound bioreactions," *Biosensors and Bioelectronics*, 22(11):2591-2597, May 2007.

Teraoka, I., et al., "Perturbation Approach to Resonance Shifts of Whispering-Gallery Modes in a Dielectric Microsphere as a Probe of a Surrounding Medium," *The Journal of the Optical Society of America B*, 20(9):1937-1946, Sep. 2003.

Vassiliev, V.V., et al., "Narrow-Line-Width Diode Laser with a High-$Q$ Microsphere Resonator," *Optics Communications*, 158(1-6):305-312, Dec. 1998.

Vollmer, F., et al., "Protein detection by optical shift of a resonant microcavity," *Applied Physics Letters*, 80(21):4057-4059, May 2002.

Yao, X.S., et al., "A Novel Photonic Oscillator," *Digest of the LEOS Summer Topical Meetings*, pp. 17-18, Aug. 1995.

Yao, X.S., et al., "A Novel Photonic Oscillator," *TDA Progress Report 42-122*, pp. 32-43, Aug. 1995.

Yao, X.S., et al., "Converting Light into Spectrally Pure Microwave Oscillation," *Optics Letters*, 21(7):483-485, Apr. 1996.

Yao, X.S., et al., "Coupled Optoelectronic Oscillators for Generating Both RF Signal and Optical Pulses," *Journal of Lightwave Technology*, 18(1):73-78, Jan. 2000.

Yao, X.S., et al., "Dual Microwave and Optical Oscillator," *Optics Letters*, 22(24):1867-1869, Dec. 1997.

Yao, X.S., et al., "Multiloop Optoelectronic Oscillator," *IEEE Journal of Quantum Electronics*, 36(1):79-84, Jan. 2000.

Yao, X.S., et al., "Optoelectronic Microwave Oscillator," *J. Opt. Soc. Am. B*, 13(8):1725-1735, Aug. 1996.

Yao, X.S., et al., "Optoelectronic Oscillator for Photonic Systems," *IEEE Journal of Quantum Electronics*, 32(7):1141-1149, Jul. 1996.

Yu, J., et al., "Compact Optoelectronic Oscillator with Ultra-Low Phase Noise Performance," *Electronics Letters*, 35(18):1554-1555, Sep. 1999.

Zamora, V., et al., "Refractometric sensor based on whispering-gallery modes of thin capillaries," *Optics Express*, 15(19):12011-12016, Sep. 2007.

International Search Report and Written Opinion dated Nov. 24, 2009 for International Application No. PCT/US2009/039559, filed Apr. 3, 2009 (7 pages).

\* cited by examiner

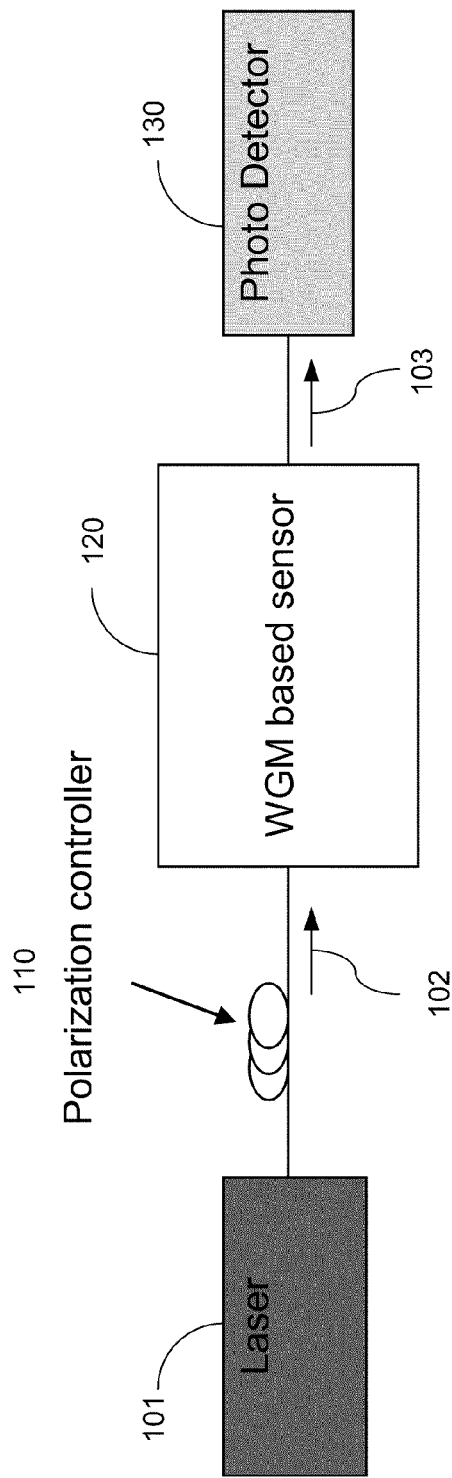
FIG. 1
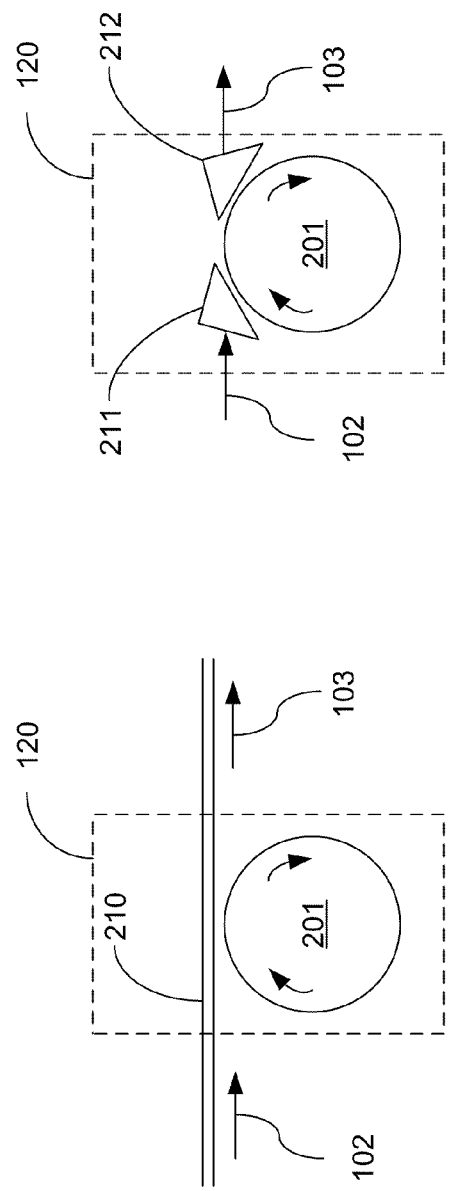
FIG. 2A
FIG. 2B

OPTICAL SENSING BASED ON OVERLAPPING OPTICAL MODES IN OPTICAL RESONATOR SENSORS AND INTERFEROMETRIC SENSORS

PRIORITY CLAIM AND RELATED APPLICATION

This patent document claims priority of U.S. Provisional Application No. 61/072,894 entitled "Thermal baseline reduction and elimination in optical resonator and interferometric sensors by differential frequency measurement of overlapping modes" and filed on Apr. 3, 2008, the disclosure of which is incorporated by reference as part of the disclosure of this document.

FEDERAL GRANT

This invention was made with government support under Contract No. NAS7-1407 awarded by National Aeronautics and Space Administration. The government has certain rights in the invention.

BACKGROUND

This patent document relates to optical sensing devices based on optical interferometers and optical resonators.

Optical sensing uses light to detect a change. Optical interferometers can be used to form optical sensors based on optical interference of light from two optical paths where a sample under measurement is placed to interact with one of the two optical paths. An optical resonator can be used to form an optical sensor that measures a shift in a resonance of the optical resonator due to a change in a surrounding sample under measurement. Optical sensors based on either optical interferometers or optical resonators can be configured in various configurations to meet the requirements of specific applications.

SUMMARY

This document describes, among others, implementations of optical sensing devices based on optical resonators and optical interferometers that use transverse magnetic (TM) and transverse electric (TE) modes to provide optical responses that, while responsive and sensitive to a change in a sample or a parameter under measurement, are insensitive to a change in temperature at an optical sensing device.

In one aspect, an optical sensing device is provided to include a laser that produces a laser probe beam and an optical resonator in an optical path of the laser probe beam to receive light of the laser probe beam in a transverse magnetic (TM) mode and a transverse electric (TE) mode and to support both TM and TE optical modes that spatially overlap. The optical resonator is located adjacent to or in contact with a sample to cause optical interaction between the sample and the light in the TM and TE optical modes. This device includes a detection unit that is coupled to the optical resonator to detect a shift in a difference between a first resonance wavelength of a TE optical mode and a second resonance wavelength of a TM optical mode to measure a change in the sample. This optical resonator may be implemented in various forms, including a whispering gallery mode resonator and a ring resonator.

In another aspect, a method is provided for optically sensing a sample and includes placing an optical resonator, which is structured to support transverse magnetic (TM) and transverse electric (TE) optical modes that spatially overlap, adjacent to or in contact with a sample the optical resonator to cause optical interaction between the sample and optical fields of light in the TM and TE optical modes; coupling probe light into the optical resonator to cause the probe light in the TM and TE optical modes to interact with the sample; and detecting a shift in a difference between a first resonance wavelength of a TE optical mode and a second resonance wavelength of a TM optical mode of the optical resonator to measure a change in the sample to reduce noise in the detected shift caused by thermal fluctuations in the optical resonator and the sample.

In another aspect, an optical sensing device includes a laser that produces a laser probe beam; an optical interferometer in an optical path of the laser probe beam to receive light of the laser probe beam in a TE mode and a TM mode and to support both TM and TE optical modes, the optical interferometer located adjacent to or in contact with a sample to cause optical interaction between the sample and the light in the TM and TE optical modes; and a detection unit that is coupled to the optical interferometer to process an optical interference signal from the optical interferometer to measure a shift in a difference between a phase shift of light in the TE mode and a phase shift of light in the TM mode to measure a change in the sample. One implementation of this optical sensing device includes an optical input module to provide laser light linearly polarized at an input polarization, and a waveguide structured to support TE and TM optical modes linearly polarized along first and second orthogonal polarizations, respectively, and located adjacent to or in contact with a sample to cause optical interaction between the sample and the light in waveguide. The waveguide is placed in an optical path of the laser light from the optical input module to receive the laser light and oriented relative to the optical input module to form a 45-degree angle between and input polarization and each of the first and second orthogonal polarizations. An output polarizer is provided to be polarized at an output polarization which is at 45 degrees with respect to each of the first and second orthogonal polarizations of the waveguide and located in an optical path of light output by the waveguide to cause optical interference between a portion of light in the TE mode from the waveguide and a portion of light in the TM mode from the waveguide. This implementation also includes a detection unit to receive light from the output polarizer to detect a difference between a phase shift of light in the TE mode and light in the TM mode in the output of the waveguide from the optical interference and to measure a change in the sample.

In yet another aspect, a method is provided for optically sensing a sample and includes placing an optical whispering gallery mode (WGM) resonator, which is structured to support TM and TE whispering gallery modes, adjacent to or in contact with a sample the WGM resonator to cause optical interaction between the sample and optical evanescent fields of light in the TM and TE whispering gallery modes. In this method, probe light is coupled into the WGM resonator to cause the probe light in the TM and TE whispering gallery modes to evanescently interact with the sample and a detection is made on the shift in a difference between a first resonance wavelength of a TE whispering gallery mode and a second resonance wavelength of a TM whispering gallery mode of the WGM resonator to measure a change in the sample to reduce noise in the detected shift caused by thermal fluctuations in the WGM resonator and the sample that shift the first resonance wavelength and the second resonance wavelength.

These and other features and implementations are described in detail in the drawings, the detailed description and the claims.

BRIEF DESCRIPTION OF THE DRAWINGS

FIG. 1 shows an example of an optical resonator sensing device based on measuring a differential frequency of the transverse magnetic (TM) and transverse electric (TE) modes in the resonator.

FIGS. 2A and 2B show two examples of whispering gallery mode (WGM) resonators as the sensing element in FIG. 1.

DETAILED DESCRIPTION

Figure 3:
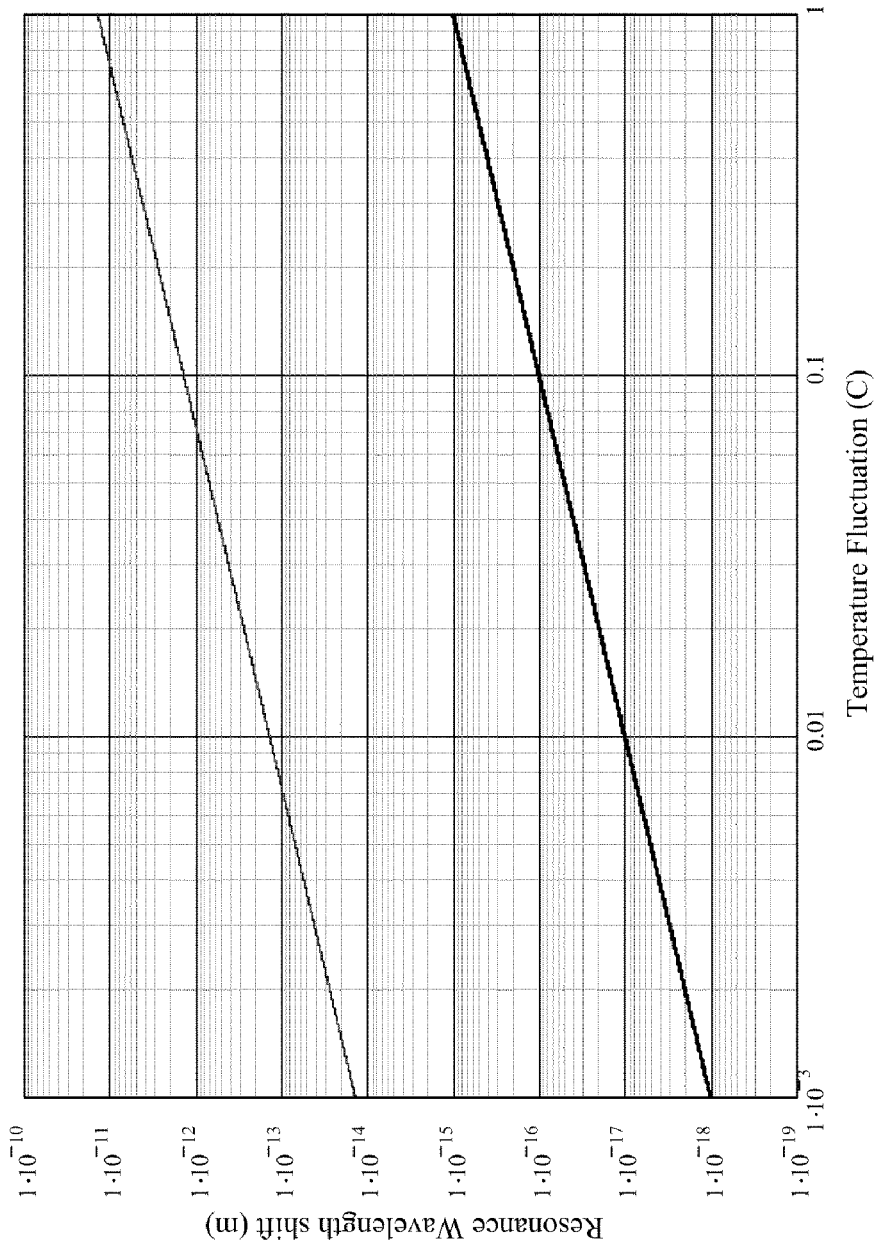
FIGS. 3, 4 and 5 show simulation and measurements of performance of the differential frequency of the TE and TM modes in WGM resonators against thermal fluctuations.

The temperature-insensitive optical sensing mechanism associated with the present techniques and optical sensing devices exploits the difference between the mode resonant frequencies of spatially overlapped transverse magnetic (TM) and transverse electric (TE) modes in an optical resonator or the difference in the phase shifts between the spatially overlapped TE and TM modes in an optical interferometer. The phase shifts in the TE and TM modes in an interferometer sensing design and the shifts in the differential frequency between the TE and TM modes in a resonator sensing design are different manifestations of changes experienced by the light. Spatially overlapped TE and TM modes in optical resonators and interferometers exhibit nearly identical changes with respect to temperature yet significant differences in sensitivity to changes in the material surrounding an optical resonator or interacting with light in an optical interferometer. Therefore, the difference between TE and TM mode frequencies or between phase shifts of the TE and TM modes is responsive and sensitive to a change in a sample or a parameter under measurement and can be used to sense the sample or measure the parameter while being insensitive to a change in temperature at the optical sensing device. In various implementations, using this difference between TE and TM mode frequencies or phase shifts between TE and TM modes for optical sensing provides a temperature-insensitive optical sensing mechanism and can lead to a practically achievable low detection limit against thermal fluctuations. In some implementations, this temperature-insensitive optical sensing mechanism can be used in combination with thermal stabilization of optical sensing devices to alleviate otherwise stringent thermal stabilization requirements associated with detection sensitivity against thermal noise. In other implementations, this temperature-insensitive optical sensing mechanism may be implemented in optical sensors without rigorous thermal stabilization.

FIG. 1 shows an exemplary optical sensing device based on the present temperature-insensitive optical sensing mechanism with an optical resonator. This optical sensing device includes a laser 101 that produces a laser probe beam 102 and an optical resonator 120 in an optical path of the laser probe beam 102 to receive light of the laser probe beam 102 in a TM mode and a TE mode and to support both TM and TE optical modes. The optical resonator 120 is located adjacent to or in contact with a sample to cause optical interaction between the sample and the light in the TM and TE optical modes. An optical polarization controller 110 may be placed in the optical path between the laser 101 and the optical resonator 120 to control the optical polarization of the probe light 102 to excite both TM and TE modes inside the optical resonator 120 at the same time. In addition, this sensing device includes a detection unit 130 that is coupled to the optical resonator 120 to receive output light 103 from the optical resonator 120 to detect a shift in a difference between a first resonance wavelength of a TE optical mode and a second resonance wavelength of a TM optical mode in response to a change in the sample. The TE and TM modes spatially overlap during their propagation inside the resonator 120 and have close angular mode numbers. The detected shift is insensitive to a change in temperature of the optical resonator 120 and the sample. This optical resonator 120 can be implemented in various forms, including a whispering gallery mode (WGM) resonator and a ring resonator.

A whispering gallery mode (WGM) resonator has a structure that confines light in a whispering gallery mode that is totally reflected within a closed circular optical path. Light in WGM resonators cannot exit the resonators by optical transmission and thus can be used to produce optical resonators with high optical quality factors that may be difficult to achieve with other optical resonators such as Fabry-Perot resonators. Light in a WGM resonator "leaks" out of the exterior surface of the closed circular optical path of the WGM resonator via the evanescence field of the WG mode. WGM resonators can be advantageously used in optical sensing devices at least in part due to their high quality factors (Q) in optical whispering gallery modes through which light is trapped within a dielectric material. For example, quality factors exceeding $10^9$ can be achieved in WGM resonators in various configurations, including disk-shaped, ring-shaped, spherical and non-spherical WGM resonators. Such high-Q WGM resonators can be fabricated in compact formats and integrated with other photonic and electronic devices over a substrate to provide various WGM resonator-based functions. A WGM resonator can be monolithically formed on a substrate (e.g., silicon substrates) to integrate with other elements as a sensing device for detecting various parameters including chemical and biological detection. In optical sensing devices based on WGM resonators, the evanescent fields of WGMs in resonators outside dielectrics strongly interact with the surrounding medium and the WGM resonance frequency is sensitive to changes in the refractive index of the surrounding medium due to the presence of chemical or biological substances, the adsorption of a molecular layer, or the attachment of a single molecule. For example, the shift of the resonance frequency of a WGM resonator is proportional to the quantitative change in the surrounding medium and can be measured to detect the change in the surrounding medium.

Referring to FIG. 1, the optical resonator 120 can be a WGM resonator based sensor with proper evanescent optical coupling. FIGS. 2A and 2B show two examples of optical evanescent coupling mechanisms for the WGM resonator in the optical sensing device in FIG. 1. In FIG. 2A, an optical waveguide 210 is provided to effectuate the proper evanescent optical coupling with a WGM resonator 201. The laser probe light 102 is guided via the waveguide 210 towards the WGM resonator 201 and is evanescently coupled into a WGM mode inside the WGM resonator 201. The same waveguide 210 also operates as an optical output coupler that evanescently couples light out of the WGM resonator 201 into the waveguide 210 as the output light 103. The waveguide 210 can be an optical fiber or a dielectric waveguide formed on a substrate.

FIG. 2B shows another example of an optical evanescent coupling mechanism for the WGM resonator in the optical sensing device in FIG. 1. An input evanescent coupler 211 is provided to receive the probe light 102 from the laser 101 and to evanescently couple the probe light 102 into the WGM resonator 201. A second, output evanescent coupler 212 is provided to evanescently couple light confined in a whispering gallery mode of the WGM resonator 201 out as the output light 103. The couplers 211 and 212 can be, for example, a tapered waveguide or a prism.

One aspect of this highly sensitive optical response of a high-Q WGM resonator is its sensitivity to a change in temperature. The temperature change can change the dimension of the WGM resonator, the refractive index of the WGM resonator and the refractive index of the surrounding medium outside the WGM resonator. Each and combination of these changes can cause a change in the resonant condition of the WGM resonator and thus changes the optical response of the WGM resonator. One adverse consequence of this sensitivity to the change in temperature of a high-Q WGM resonator is the noise associated with thermal fluctuations and such noise can limit the practical detection sensitivity of the high-Q resonator. Such thermal noise in connection with a high-Q WGM resonator can be suppressed by using one or more thermal stabilization mechanisms, e.g., passive and active thermal stabilization mechanisms.

The present temperature-insensitive optical sensing mechanism based on measuring the difference between the TE and TM mode resonant frequencies of the WGM resonator suppresses the thermal noise without relying on any thermal stabilization while maintaining the sensitive detection due to the high Q factor of the WGM resonator. In some implementations of optical sensing devices based on the present temperature-insensitive optical sensing mechanism, passive and active thermal stabilization mechanisms may also be provided.

In a WGM resonator, the individual TE or TM resonances and the differential frequency between the TE and TM resonances are shifted by the both effects of the change in condition of surrounding environment (e.g., refractive index, absorption of chemical or biological substances) and the temperature fluctuations in both the surrounding environment and the WGM resonator. The noise associated with temperature fluctuations can be a significant limitation to and may practically be the leading limiting factor in the detection sensitivity for WGM resonator sensors. However, when the TE and TM modes spatially overlap, the effects caused by the thermal fluctuations on both the TE and TM resonances are substantially the same and thus are canceled out in the differential frequency between the TE and TM resonances. As such, the differential frequency between the TE and TM resonances carries the information of the changes in the condition of the surrounding environment and does not change with thermal fluctuations. An analysis of the thermal shifts to TE and TM resonances in a WGM resonator is provided to below.

The WGM wavelength resonance is related to the effective refractive index of the WGM resonator as $$l = \frac{2\pi R n_{eff}}{\lambda}$$

where l is an integer that describes the WGM angular mode number. The resonance wavelength has a dependence on the temperature T given by:

$$\frac{\Delta \lambda}{\lambda} = \frac{\partial R}{\partial T} \cdot \frac{1}{R} \Delta T + \frac{\partial n_{eff}}{\partial T} \cdot \frac{1}{n_{eff}} \Delta T$$
$$= \frac{\partial R}{\partial T} \cdot \frac{1}{R} \Delta T + \frac{\partial n_{eff}}{\partial n_{resonator}} \cdot \frac{\partial n_{resonator}}{\partial T} \cdot \frac{1}{n_{eff}} \Delta T,$$

where $$\alpha = \frac{\partial R}{\partial T} \cdot \frac{1}{R}$$

is the thermal expansion coefficient and $$\alpha_n = \frac{\partial n_{resonator}}{\partial T}$$

is thermo-optic coefficient of the bulk material of the WGM resonator.

For the TE mode, the resonance wavelength has a dependence on the temperature T given by $$\frac{\Delta \lambda}{\lambda}\bigg|_{TE} = \frac{\partial R}{\partial T} \cdot \frac{1}{R} \Delta T + \frac{1}{1 + \frac{\alpha_p}{6}\left(\frac{\lambda_{TE}}{\pi R n_{eff\_TE}}\right)^{2/3}} \cdot \frac{\partial n_{resonator}}{\partial T} \cdot \frac{1}{n_{eff\_TE}} \Delta T.$$

For the TM mode, the resonance wavelength has a dependence on the temperature T given by $$\frac{\Delta \lambda}{\lambda}\bigg|_{TM} = \frac{\partial R}{\partial T} \cdot \frac{1}{R} \Delta T + \frac{1}{1 + \frac{\alpha_p}{6}\left(\frac{\lambda_{TM}}{\pi R n_{eff\_TM}}\right)^{2/3}} \cdot \frac{\partial n_{resonator}}{\partial T} \cdot \frac{1}{n_{eff\_TM}} \Delta T.$$

The differential between the TE and TM resonances is:

$$\Delta \lambda_{TM} - \Delta \lambda_{TE} = \left(\frac{\lambda_{TM}}{1 + \frac{\alpha_p}{6}\left(\frac{\lambda_{TM}}{\pi R}\right)^{2/3} n_{eff\_TM}^{1/3}} - \frac{\lambda_{TE}}{1 + \frac{\alpha_p}{6}\left(\frac{\lambda_{TE}}{\pi R}\right)^{2/3} n_{eff\_TE}^{1/3}}\right) \alpha_n \Delta T.$$

Because of the slightly difference in effective refractive indices of TE and TM modes, the above equations indicate that the difference of resonance wavelength shifts due to a temperature fluctuation, or perturbation by the change in surrounding refractive index or absorption of a thin layer of molecules. For example, the thermal expansion coefficient of fused silica is about $5 \times 10^{-7}/^\circ$ C. which is two orders of magnitude smaller than the effect of the thermo-optics coefficient of $1.2 \times 10^{-5}/^\circ$ C. in fused silica. In practical estimation, the thermal expansion dependence term in the above equations may be ignored.

The above equations can be further simplified to provide more specific relationships for the TE and TM resonance frequencies. Assume n is the refractive index of the material for the optical resonator, no is the refractive index of the surrounding medium and $\alpha_{out}=\partial n_o/\partial T$ is the thermo-optics coefficient for the surrounding medium. The resonance frequencies for the TE and TM modes and their differential are $$\left.\frac{\Delta\omega_{TE}}{c}\right|_{Temp} \cong \qquad (6)$$

$$\frac{1}{R}\left(\frac{n}{(n^2-n_o^2)^{3/2}} - \frac{1}{n^2}\left[\nu + \alpha_q\left(\frac{\nu}{2}\right)^{1/3} + \frac{3\alpha_q^2}{20}\left(\frac{2}{\nu}\right)^{1/3}\right]\right)\alpha_n\Delta T +$$

$$\left.\frac{1}{R}\left(\frac{n_0}{(n^2-n_o^2)^{3/2}}\right)\alpha_{out}\Delta T, \frac{\Delta\omega_{TM}}{c}\right|_{Temp} \cong$$

$$\frac{1}{R}\left(\frac{n_o^2(3n^2-2n_o^2)}{n^3(n^2-n_o^2)^{3/2}} - \frac{1}{n^2}\left[\nu + \alpha_q\left(\frac{\nu}{2}\right)^{1/3} + \frac{3\alpha_q^2}{20}\left(\frac{2}{\nu}\right)^{1/3}\right]\right)\alpha_n\Delta T +$$

$$\left.\frac{1}{R}\left(\frac{n_o}{(n^2-n_o^2)^{3/2}}\left[2 - \frac{n_o^2}{n^2}\right]\right)\alpha_{out}\Delta T, \frac{(\Delta\omega_{TE}-\Delta\omega_{TM})}{c}\right|_{Temp} \cong$$

$$\frac{1}{Rn}\left(\frac{1 - 2\frac{n_o^2}{n^2}}{\sqrt{n^2-n_o^2}}\right)\alpha_n\Delta T + \frac{1}{Rn^2}\left(\frac{n_o}{\sqrt{n^2-n_o^2}}\right)\alpha_{out}\Delta T.$$

FIG. 3 shows the resonance wavelength shift due to temperature fluctuations for individual TE mode (red) and TM mode (blue) and the change of the differential wavelength of two resonance modes (black). The resonance wavelength shift of each mode TE or TM due to the temperature fluctuation is about 4 orders of magnitude higher than the change of the differential wavelength of two resonance modes TE and TM (i.e., the change in the resonance wavelength of TE mode minus the change in resonance wavelength of TE mode). Therefore, the change in differential resonance wavelength of TE and TM mode is practically immune to the temperature fluctuation.

Figure 4:
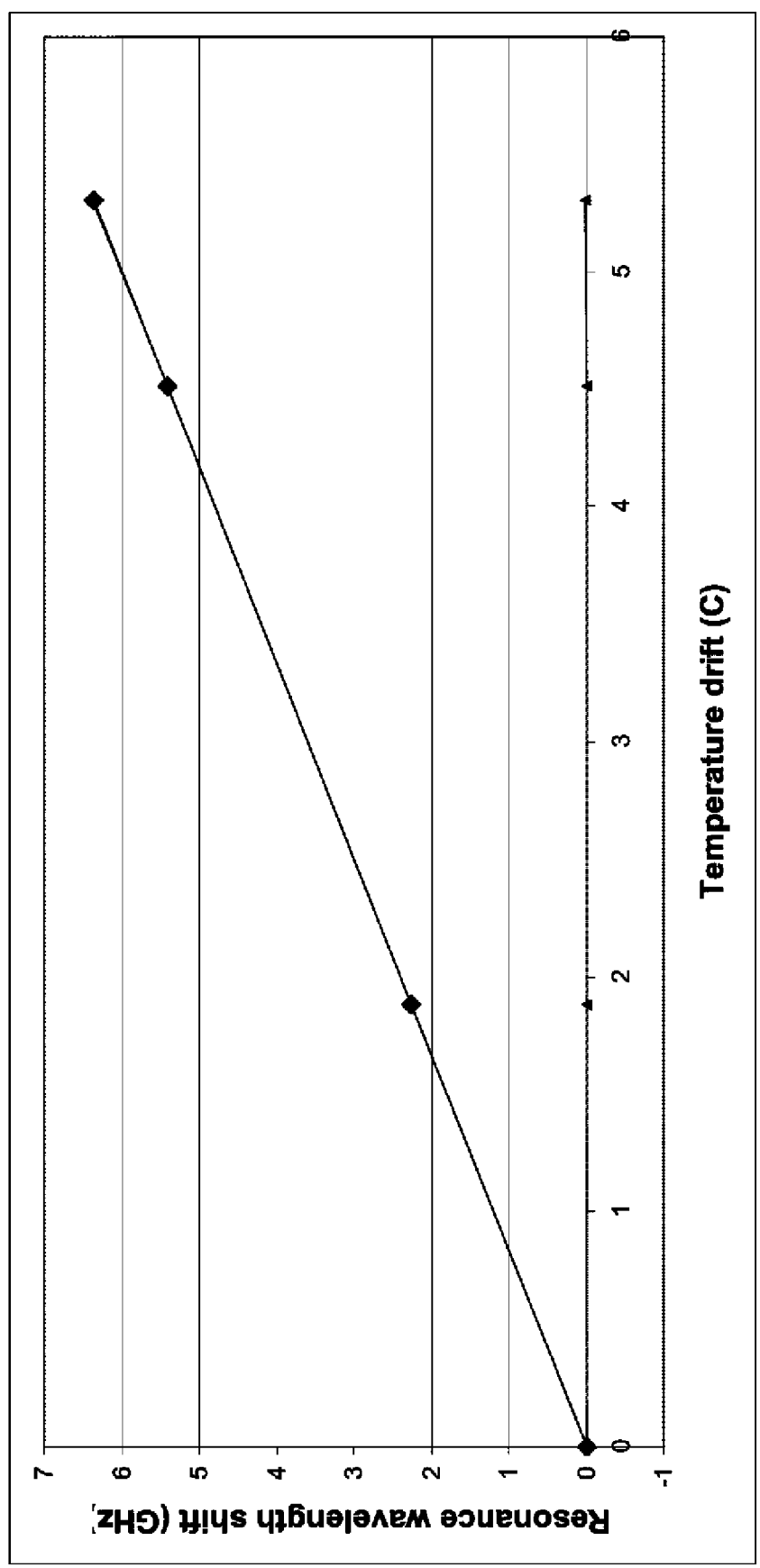

FIG. 4 shows measured resonant wavelength shifts of individual TE and TM modes and the differential frequency between the TE and TM modes caused by the temperature using a WGM resonator based sensing device in FIG. 1. The measurements suggest that the drift of the differential frequency between TE mode and TM mode is very small under the effect of temperature fluctuation, about four orders of magnitude lower than the drift of each individual resonant frequency of the TE or TM mode. Therefore, the measurement of the differential frequency between the TE mode and TM mode allows detection of a small change in the refractive index of the surrounding medium or very low concentration of chemical or biological samples outside the WGM resonator.

Consider an example of using such a sensor to detect a uniform change in the refractive index of a surrounding medium outside the WGM resonator. The change of the surrounding refractive index affects on the shifts of each individual resonant wavelength can be computed by the following:

$$\left.\frac{\Delta k}{k_0}\right|_{TE} = -\frac{n_o\Delta n_o}{(n_{resonator}^2-n_o^2)^{3/2}}\frac{1}{k_0R},$$

-continued $$\left.\frac{\Delta k}{k_0}\right|_{TM} = -\frac{n_o\Delta n_o}{(n_{resonator}^2-n_o^2)^{3/2}}\frac{1}{k_0R}\left(2 - \frac{n_o^2}{n_{resonator}^2}\right),$$

where $$k_0 = \frac{2\pi}{\lambda},$$

$n_{resonator}$ is the refractive index of the material of the WGM resonator and $n_o$ is refractive index of the surrounding medium. The differential shift as a function of the change in the surrounding medium refractive index is $$\Delta k_{TM} - \Delta k_{TE} = \frac{1}{R}\frac{n_o\Delta n_o}{(n_{resonator}^2-n_o^2)^{3/2}}\left(\frac{n_o^2}{n_{resonator}^2} - 1\right).$$

Figure 5:
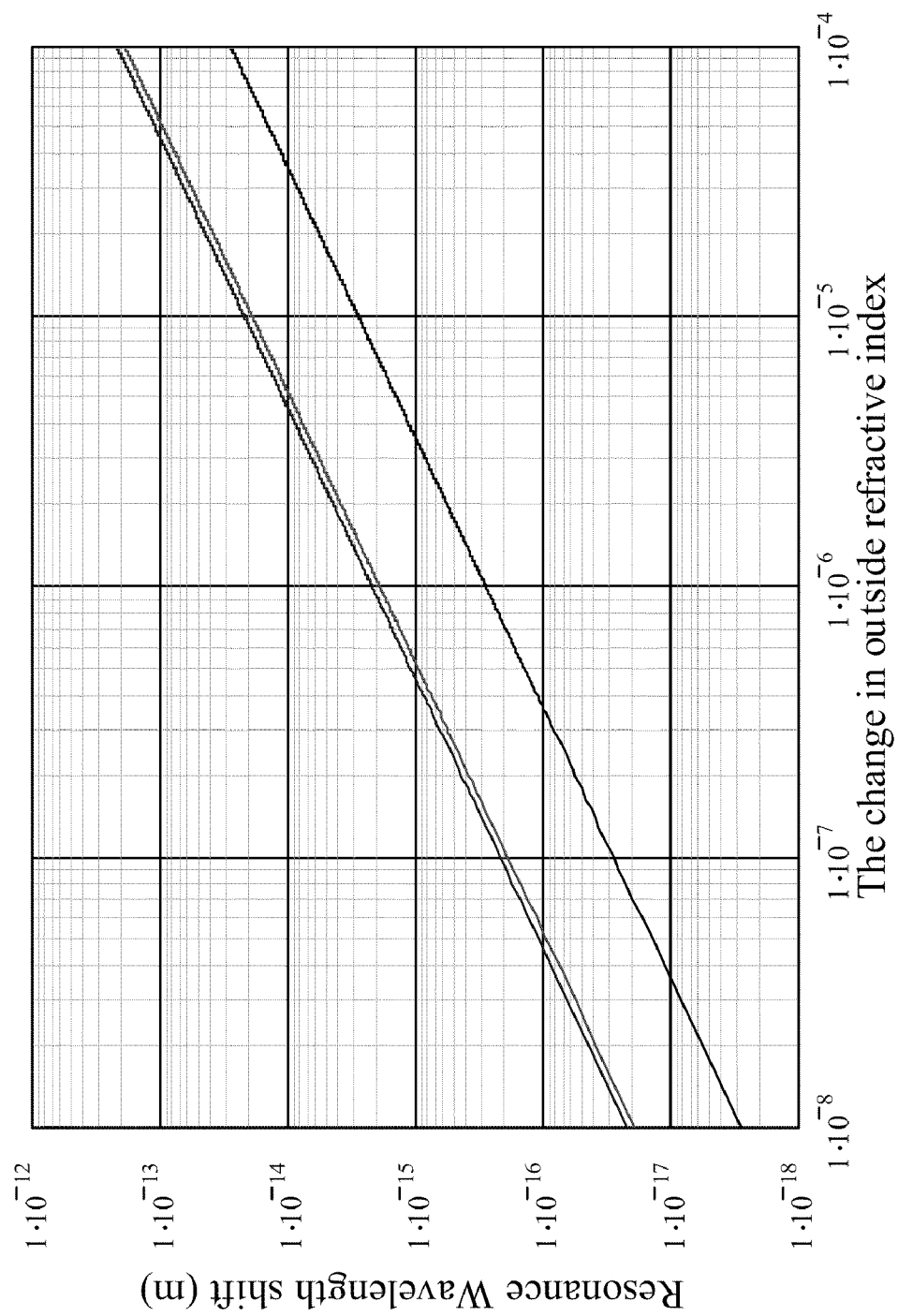

FIG. 5 shows the resonance wavelength shift due to the change in the refractive index of the surrounding medium for individual TE and TM modes (red and blue) and the change of the differential wavelength of two resonance modes (black). The data in FIG. 5 shows that the differential detection sensitivity is only reduced by a factor of ten while the thermal drift is reduced by a factor of $10^4$. The effective signal to background drift is improved by about three orders of magnitude.

In addition, consider the effect of a temperature fluctuation of about 0.01° C. at the room temperature on the TE and TM modes of the WGM resonator. This fluctuation causes each individual TE or TM mode to fluctuate about $10^{-13}$ m around a resonant peak and the differential frequency to fluctuate in the range of $10^{-17}$ m. Therefore, using the differential frequency between the TE and TM modes can detect a change of the surrounding refractive index in the range of $10^{-8}$ instead of about $10^{-5}$ if the wavelength shift of each individual TE or TM mode were used.

Figure 6:
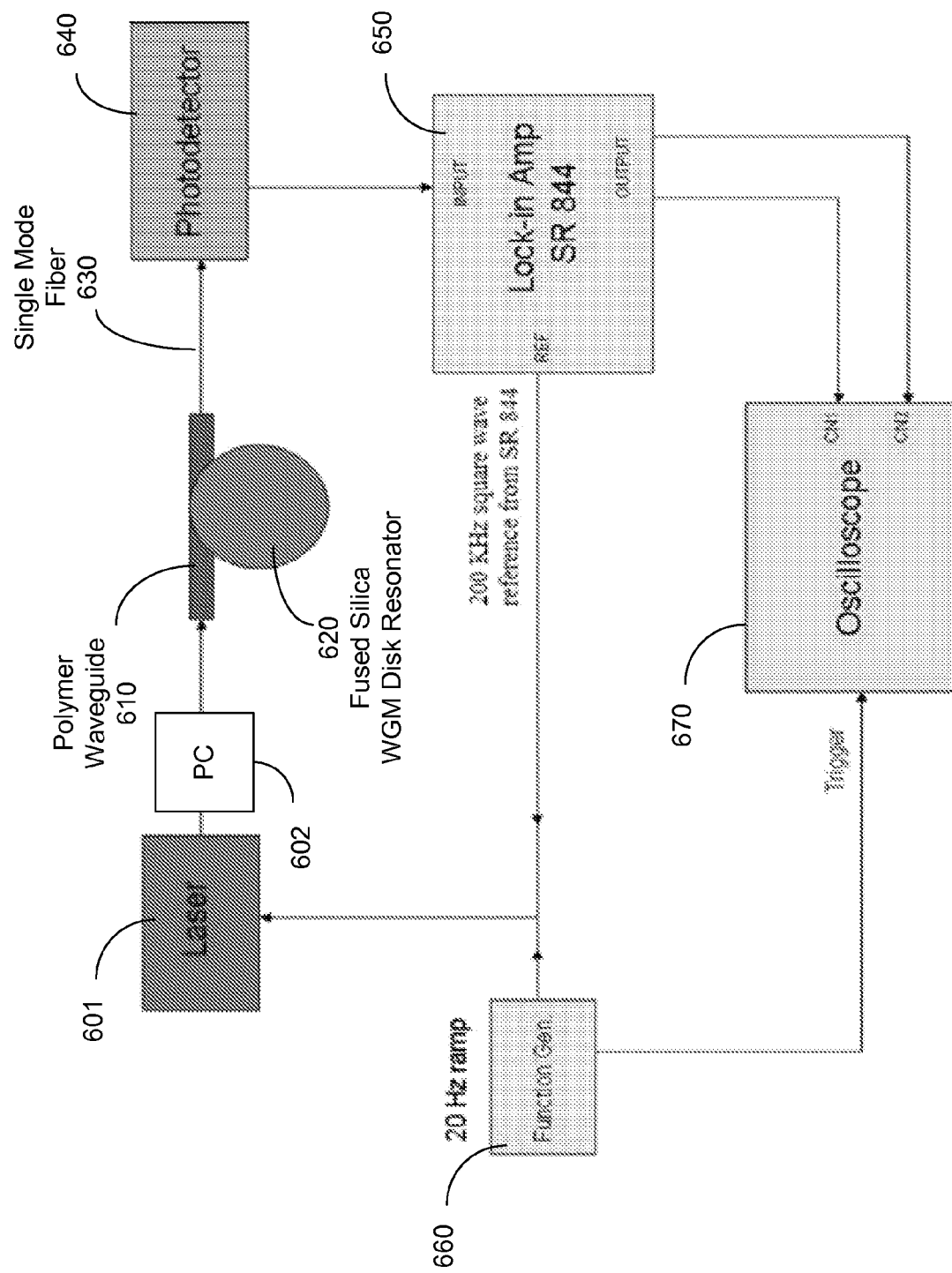
FIG. 6 shows a measurement system for measuring performance of the differential frequency of the TE and TM modes in a fused silica WGM resonator.

FIG. 6 shows a system that was used to measure thermal dependencies of TE and TM modes of a high Q WDM disk resonator 620 made of fused silica with a radius of 1.6 mm. A tunable 1550-nm laser 601 is used to produce laser light for the measurements. The laser light is first directed to pass through a polarization controller 602 which controls the polarization of the laser light. The laser light output from the polarization controller 602 is coupled into a polymer waveguide 610 that is vertically coupled to the fused silica disk resonator. The waveguide 610 is designed to provide the proper phase matching condition for the evanescent optical coupling with the disk resonator 620 to excite the fundamental whispering gallery mode near the edge of the disk resonator 620. The waveguide 610 is used as both an input coupler for coupling the polarization-controlled laser light from the polarization controller 602 into the disk resonator 620 and an output coupler for coupling laser light in the disk resonator 620 out of the disk resonator 620 as a resonator transmission signal. The resonator transmission signal from the disk resonator 620 is directed along the waveguide 610 to a single mode fiber 630 which is butt coupled to the end facet of the waveguide 610. A photodetector 640 is coupled to the single mode fiber 630 to detect the resonator transmission signal from the disk resonator 620.

To perform measurements, the polarization controller 602 is operated and adjusted to enable simultaneous excitation of both TE and TM polarization resonances in the disk resonator 620. The differential frequency shift between the set of TE and TM modes with the same angular mode numbers were measured to detect the temperature fluctuation or a change in the refractive index of the surrounding medium outside the disk resonator 620. All components were enclosed inside a box to avoid temperature fluctuations of the room air without using an active thermal control. The frequency of the coupling peaks in the transmission spectrum of the disk resonator 620 can be difficult to be precisely measured because the minima of these resonance peaks are rounded and do not have a pronounced minimal dip. To address this, the detector output from the photodetector 640 is directed into a lock-in amplifier 650 to obtain the derivative of the transmission signal and to track its zero crossing point. As a consequence of the relatively large slope and crossing zero at one point of the derivative signal, small temperature fluctuations or small variations in the refractive index of the medium surrounding the disk resonator 620 can thereby be transformed into a detectable signal. The measurement system also includes a ramp signal function generator 660 to sweep the laser frequency, an oscilloscope 670, and a computer to observe and record the transmission spectrum.

During measurements, the fused silica disk resonator 620 was heated by illuminating the surface with light from a lamp to introduce thermal shifts of individual TE and TM modes of the disk resonator 620 and the difference frequency of the TE and TM modes was recorded. The temperature of the disk resonator 620 was increased up to 5° C. above the normal room temperature by increasing the power of the lamp. Each measurement was taken after the temperature of the disk resonator 620 was stabilized. The stability of the temperature due to the heating by the light from the lamp at equilibration is ±0.05° C.

Figure 7:
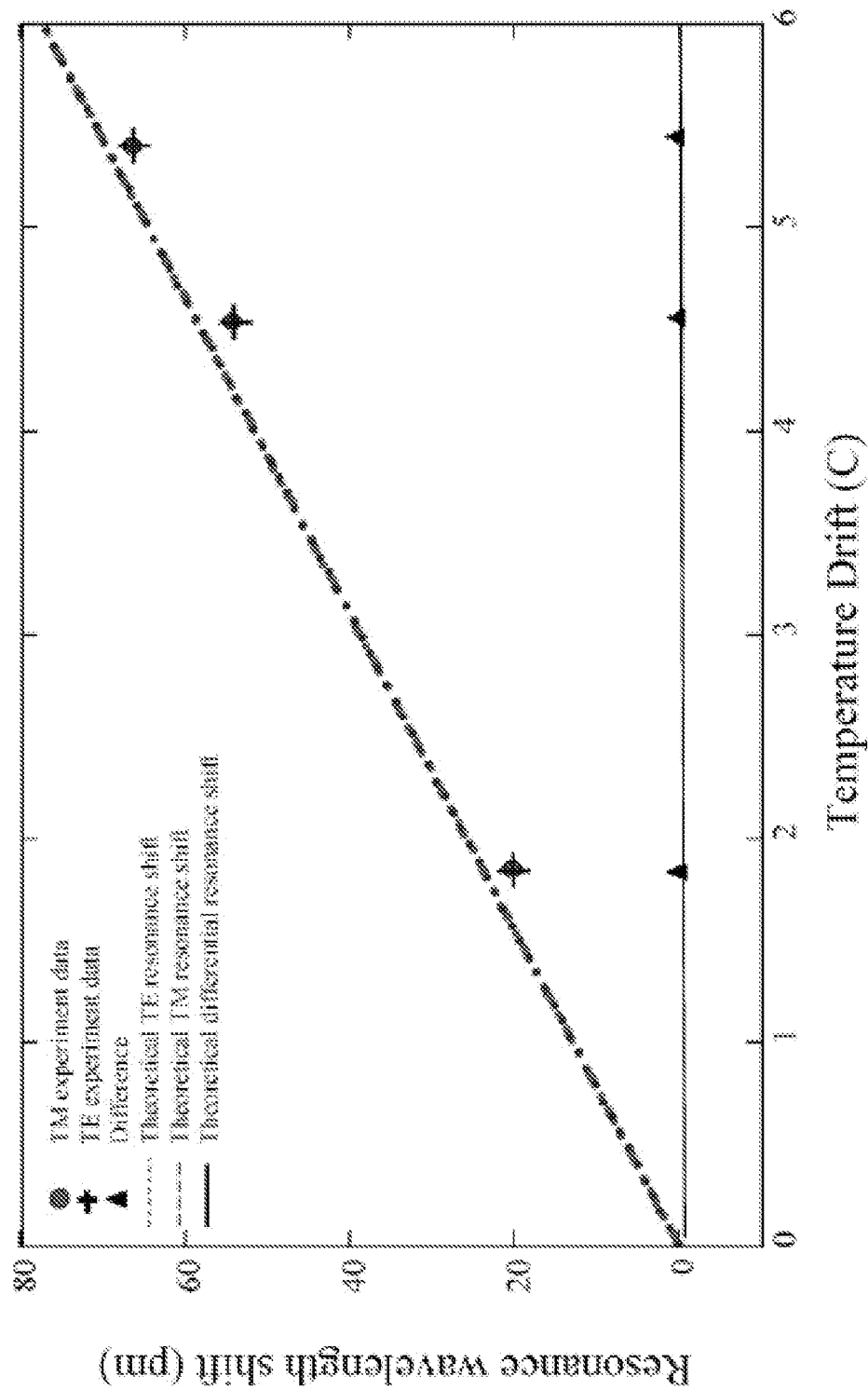
FIGS. 7, 8 and 9 show measurements made by using the differential frequency of the TE and TM modes in fused silica WGM resonators.

FIG. 7 shows measured data for the resonant frequency shift of the TE mode, the TM mode, and the difference as a function of temperature. The plot represents theoretical calculation and is provided along with measured data for the resonance shift of each individual TE and TM mode, and the change of the differential frequencies when the temperature is changed by 5° C. Crosses, dots, and triangles correspond to TE and TM resonance shifts and the differences, respectively. The dash, dot, and solid curves are the theory prediction of individual TM and TE resonant frequency shifts and the difference. The uncertainty of the TM or TE resonance mode shift is ±0.65 pm. The observed changes in the differential frequency were within the detection sensitivity of ±0.05 pm of the measurement setup. Our calculation result for the differential resonance shift is about 0.001 pm when the temperature change is 5° C.

Measurements were also conducted by placing the disk resonator in contact with a glucose solution and by detecting the change in the surrounding solution's refractive index. The resonator surface was covered by a glucose solution which has a refractive index that varies linearly with the concentration of glucose in water as $1.4 \times 10^{-3}$ refractive index unit (RIU)/wt. %. After each measurement with different glucose concentrations, the disk resonator was rinsed and cleaned with DI water. The output transmission spectrum was recorded after the system was stabilized. All measurements were repeated four times to reduce the measurement errors. The glucose solutions used had glucose concentrations of 0.033 wt. %, 0.5 wt. %, and 1 wt. %, corresponding to values for the refractive index for the surrounding medium outside the resonator of 1.32505, 1.3257, and 1.3264, respectively. The glucose concentration is measured by the weight percent (wt. %) of glucose in deionized (DI) water. Measurements on the shift of TE and TM resonance peaks and the difference through the transmission spectrum of the device were conducted and compared to the spectra of DI water with a refractive index of about 1.325 as a reference point.

Figure 8:
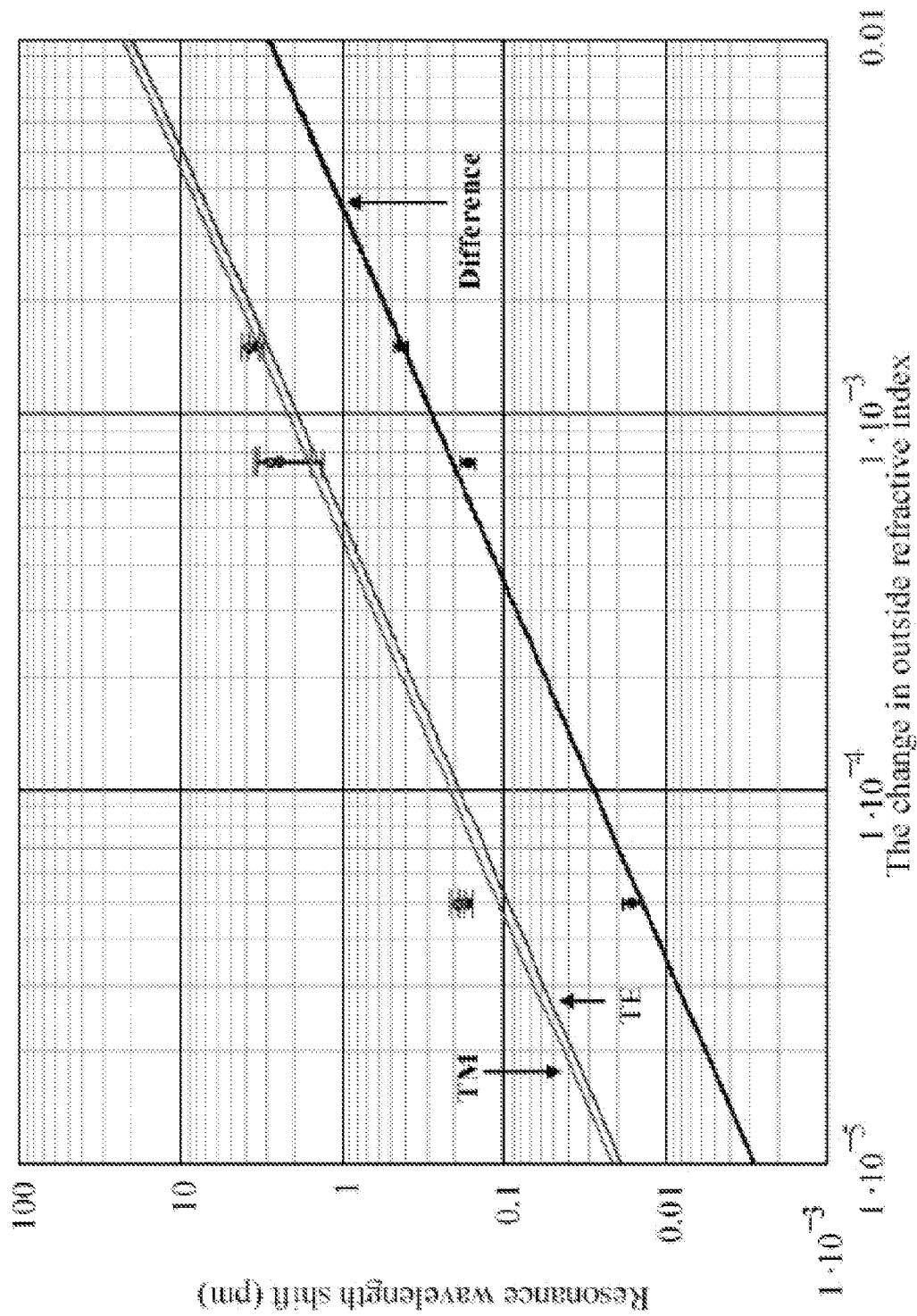

FIG. 8 shows the experimental averaged resonance frequency shifts and weighted error bars for TE and TM resonance peaks and the difference versus the change in the surrounding refractive index as calculated for the three glucose solutions used in the measurements. The thermal fluctuation causes a significant uncertainty in resonant frequency shifts of individual TE and TM modes, while the uncertainty of correlated differential frequency measurement is significantly reduced. Therefore, the use of the differential frequency between the TE and TM resonant frequencies provides an enhanced detection limit.

Figure 9:
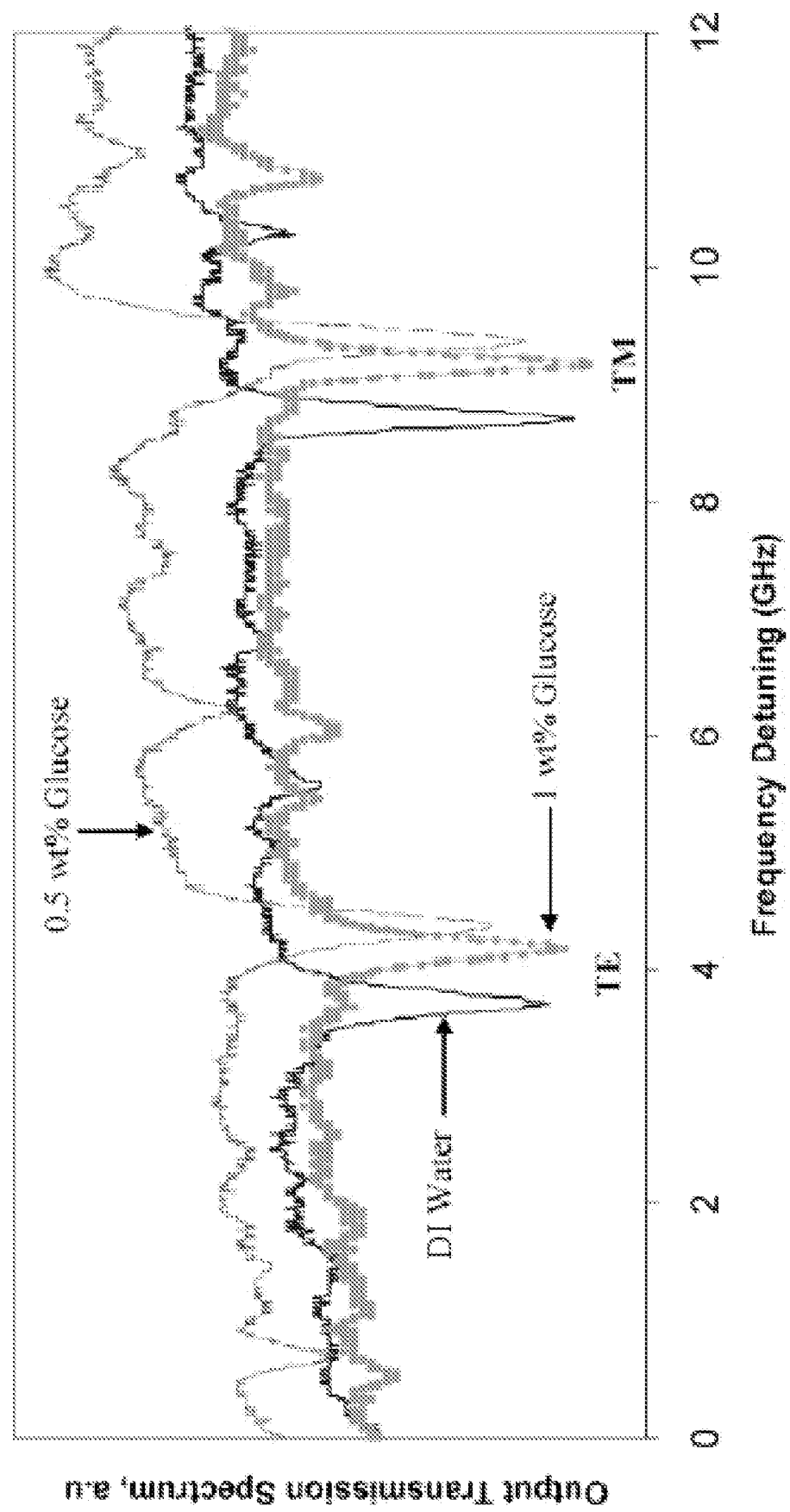

FIG. 9 shows measurements of detection of glucose solution samples to illustrate the advantage of using the difference frequency measurements. The measured shifts of the TE or TM resonances as shown are unreliable due to the thermal noise caused by the thermal fluctuations because, for example, the measured shift for the 0.5 wt. % solution is more than the measured shift for the 1.0 wt. % solution. In comparison, the measured difference in the resonant frequencies is free of such inconsistency caused by the temperature drift during the measurements. Based on the results, a temperature fluctuation of 1° C. would correspond to a detection limit of $9.8 \times 10^{-5}$ in a change of the RIU in the aqueous surrounding medium's refractive index by using the differential measurement and a detection limit of $5.6 \times 10^{-3}$ in a change of the RIU by directly measuring TE or TM resonance frequency. Therefore, the present differential measurement technique provides a means to achieve a low detection limit under ambient temperature fluctuation. The frequency deviation due to effects of thermal expansion and thermoelastic fluctuation for both TE and TM modes are significantly suppressed.

The above examples use a WGM resonator as an optical resonator sensor to illustrate the technique of measuring the differential frequency of the TE and TM resonances with suppressed thermal noise in optical sensing. Other optical resonators that simultaneously support spatially overlapped TE and TM modes can also be used to implementing the technique.

Figure 10:
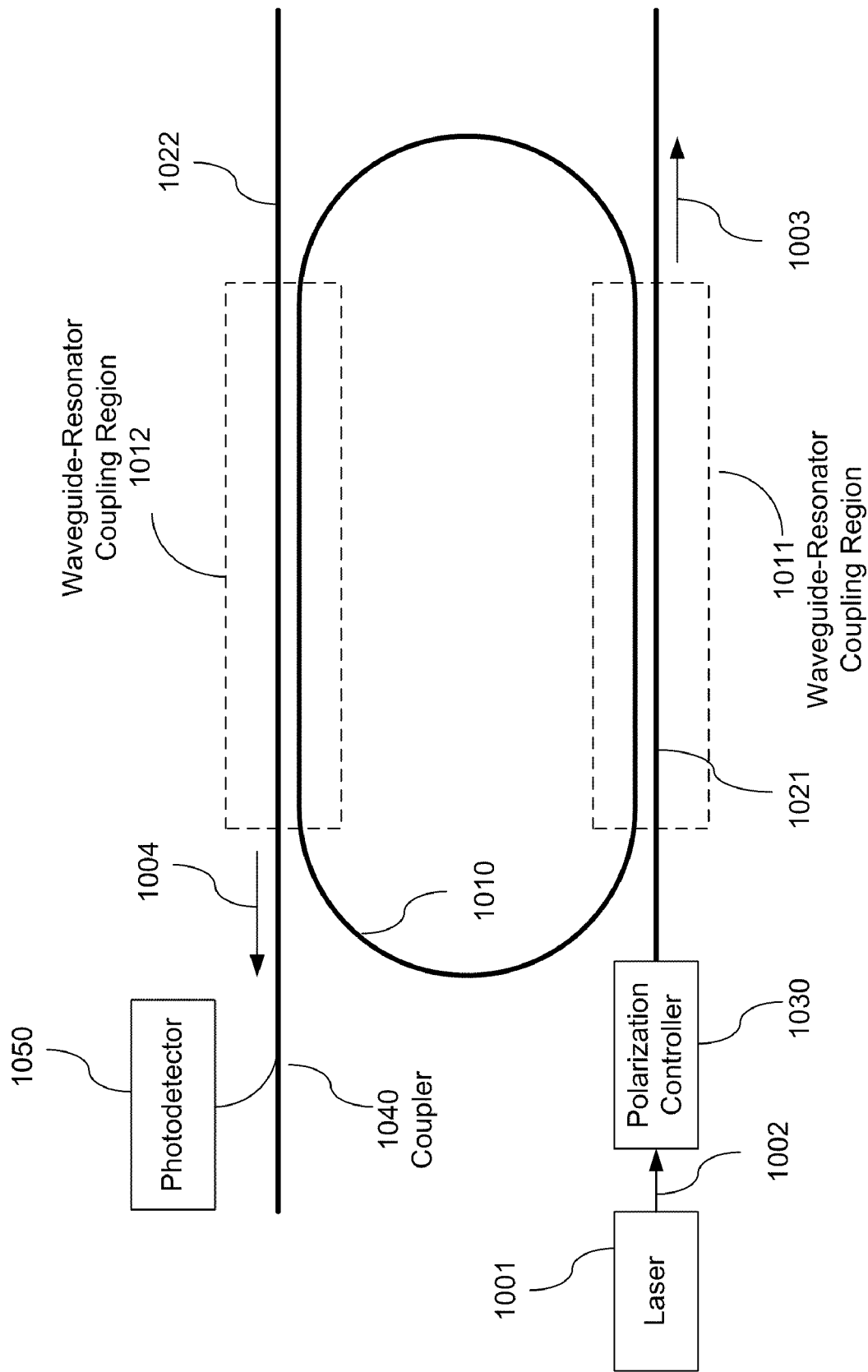
FIG. 10 shows an example of a waveguide resonator sensor based on the of the differential frequency of spatially overlapped TE and TM modes in a ring resonator.

For example, FIG. 10 shows an optical waveguide resonator sensor that uses a waveguide ring resonator 1010 coupled with two waveguides 1021 and 1022 to measure the differential frequency of the TE and TM resonances for sensing applications. A laser 1001 is used to produce laser light 1002 which is coupled into the waveguide 1021 to excite both TE and TM modes inside the ring resonator 1010 that spatially overlap. A polarization controller 1020 may be provided to control the polarization of the laser light coupled into the waveguide 1021 to facilitate the excitation of both TE and TM modes inside the ring resonator 1010. The ring resonator 1010 can have two waveguide-resonator coupling regions 1011 and 1012 that are structured to provide evanescent coupling with the two waveguides 1021 and 1022, respectively. The optical waveguides 1021 and 1022 and the waveguide ring resonator 1010 can be monolithically integrated on a substrate such as a silicon substrate.

The laser light 1002 coupled into the waveguide 1021 is coupled into the ring resonator 1010 in the coupling region 1011 and the light inside the ring resonator 1010 is coupled out at the coupling region 1012 into the waveguide 1022 as the first output 1004 and at the coupling region 1011 as the second output 1003. An optical detector 1050 can be coupled to receive light of the optical output 1004 by either being directly coupled to the waveguide 1022 to receive the output 1004 or receiving a portion of the output 1004 via a coupler 1040 that is coupled to the waveguide 1022 to split the portion from the waveguide 1022.

In operation, a target sample is placed in contact with the ring resonator 1010 to optically interact with light in the TE and TM modes of the ring resonator 1010. This interaction with the target sample causes shifts in the resonances of the spatially overlapped TE and TM modes. The target sample, like in other optical sensing devices described in this document, can be a gas, a liquid, a gel, or a solid medium. The measured shift in the differential frequency of the TE and TM modes can be used to detect a change in the target sample, such as a change in a concentration of a substance in the target sample or a presence of a material in the target sample. In some sensing applications such as in detecting biological targets, the surface of the ring resonator 1010 and resonators in other optical sensing devices described in this document can be functionalized as a biologically functional surface to selectively bond with specific target cells or target molecule groups.

In addition to resonator sensors and optical waveguide resonator sensors described above, the present technique of measuring the differential frequency of the TE and TM modes with suppressed thermal noise in optical sensing can be implemented in waveguide interferometric sensors in which the TE and TM modes propagating along the same optical path and spatially overlapping with each other form two optical arms of the interferometer for such a waveguide interferometric sensor. A waveguide interferometric sensor can include a laser that produces a laser probe beam, and an optical interferometer in an optical path of the laser probe beam to receive light of the laser probe beam in a TE mode and a TM mode and to support both TM and TE optical modes. The optical interferometer is located adjacent to or in contact with a sample to cause optical interaction between the sample and the light in the TM and TE optical modes. This sensing device includes a detection unit that is coupled to the optical interferometer to process an optical interference signal from the optical interferometer to measure a shift in a difference between a phase shift of light in the TE mode and a phase shift of light in the TM mode to measure a change in the sample.

Figure 11:
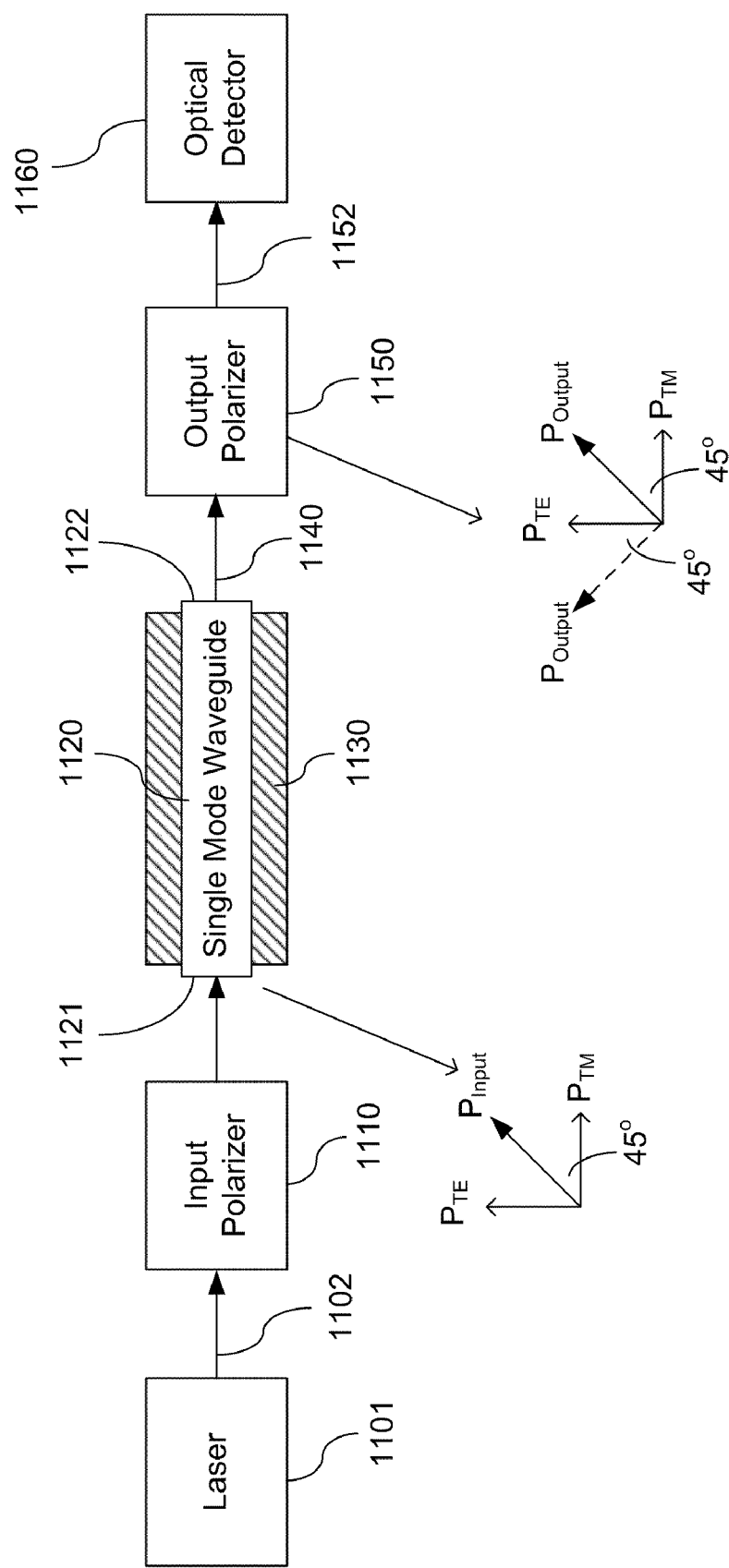
FIG. 11 shows one example of a waveguide interferometric sensor where a single mode waveguide is used to support spatially overlapped TE and TM modes for the optical sensing operation.

FIG. 11 shows one example where a single mode waveguide is used to support TE and TM modes for the optical sensing operation in a waveguide interferometric sensor. As illustrated, a laser 1101 is used to produce laser light 1102 for sensing. A single mode waveguide 1120 is provided and is structured to support two orthogonally polarized TE and TM optical modes and the exterior surface of the waveguide 1120 is in contact with a target sample 1130 under measurement so that the light in the TE and TM modes guided by the waveguide 1120 interacts with the target sample 1130 to cause phase shifts in the light of the TE and TM modes. The laser light 1102 is coupled into the waveguide 1120 at the input port 1121 with its polarization at 45 degrees with respect to the TE and TM polarizations ($P_{TE}$ and $P_{TM}$). This input optical configuration allows both TE and TM modes with equal amplitudes to be generated inside the waveguide 1120 from the input light 112. The light in the TE mode and the light in the TM mode propagate along the same waveguide 1120 and spatially overlap with each other. However, the TE and TM modes are independent from each other and do not optically interfere due to their mutually orthogonal polarizations. A polarization controller, a waveplate or an input polarizer 1110 may be placed upstream from the input port 1121 of the waveguide 1120 to control the polarization of the laser light 1102 at the above polarization orientation. The light in both TE and TM modes passes through the waveguide 1120 and undergoes phase changes via this interaction and the propagation from the input port 1121 to the output port 1122 of the waveguide 1120. The output light 1140 from the waveguide 1120 carries information of the target sample 1130 and is directed into an output polarizer 1150 and the transmission 1152 of the output polarizer 1150 is directed into a photodetector 1160 for processing.

The output polarizer 1150 is oriented to have its polarization direction at 45 degrees with the TE and TM polarizations of the waveguide 1120 and thus can be either parallel or perpendicular to the polarization of the input polarizer 1110 as illustrated in the possible two output polarization directions for the output polarizer 1150. The components of the polarizations of the TE and TM modes along the output polarizer 1150 can optically interfere with each other and thus produce an interference pattern that represents the phase shifts of the TE and TM modes when light passes through waveguide 1120. Therefore, the change of refractive index of the waveguide 1120, the surrounding medium 1130, and in the case of an adsorption of biomolecules, the refractive index of the adsorbate layer, or the change of refractive indices due to the effect of temperature fluctuation induce phase shifts in the transmitted light out of the waveguide 1120 in both TE and TM modes. After passing through the output polarizer 1150, the transmitted light in the TE mode and the transmitted light in the TM mode polarized along the polarization of the output polarizer 1150, interfere with each other so that the light received by the optical detector 1160 reflects the differential changes in the phase shifts in the TE and TM modes. The TE and TM modes have nearly identical changes with respect to the temperature due to the spatial overlap of the TE and TM modes in their passage through the waveguide 1120. Thus the effect on the TE and TM modes due to thermal fluctuations or variations in the waveguide 1120 is essentially canceled in the differential changes detected by the optical detector 1160. The TE and TM modes have significant differences in sensitivity to changes in the material surrounding the waveguide 1120 and such differences are reflected in the light received by the optical detector 1160 and are measured. Therefore, the use of the single waveguide 1120 as the sensing region for spatially overlapped TE and TM modes to interact with surrounding medium for sensing leads to a practically achievable low detection limit in the presence of temperature changes.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. However, variations and enhancements of the described implementations and other implementations can be made based on what is described and illustrated in this document.

What is claimed is:

1. An optical sensing device, comprising:
a laser that produces a laser probe beam;
an optical resonator in an optical path of the laser probe beam to receive light of the laser probe beam in a transverse magnetic (TM) mode and a transverse electric (TE) mode and to support both TM and TE optical modes that spatially overlap, the optical resonator located adjacent to or in contact with a sample to cause optical interaction between the sample and the light in the TM and TE optical modes; and
a detection unit that is coupled to the optical resonator to detect a shift in a difference between a first resonance wavelength of a TE optical mode and a second resonance wavelength of a TM optical mode and to measure a change in the sample from the detected shift.

2. The device as in claim 1, comprising:
an optical polarization controller located in the optical path between the laser and the optical resonator to control an optical polarization of the laser probe beam at the optical resonator for coupling the light of the laser probe beam into light of the TM and TE optical modes inside the optical resonator.

3. The device as in claim 1, wherein:
the detection unit includes a photodetector that receives light from the optical resonator.

4. The device as in claim 1, wherein:
the detection unit processes the detected shift to measure a change in a refractive index of the sample.

5. The device as in claim 1, wherein:
the detection unit processes the detected shift to measure a change in a concentration of a substance in the sample.

6. The device as in claim 1, comprising:
an optical coupler optically coupled to the optical resonator to evanescently couple light of the laser probe beam into the optical resonator.

7. The device as in claim 1, wherein:
the optical resonator is a whispering gallery mode (WGM) resonator and the TE and TM optical modes are TE and TM whispering gallery modes, respectively.

8. The device as in claim 1, wherein:
the optical resonator is a ring resonator.

9. The device as in claim 8, wherein:
the ring resonator comprises an optical waveguide forming a closed ring.

10. The device as in claim 9, wherein:
the optical waveguide is an optical waveguide integrated on a substrate.

11. The device as in claim 9, comprising:
a separate waveguide located adjacent to the ring resonator to be in evanescent coupling with the ring resonator to provide optical coupling with the ring resonator.

12. The device as in claim 1, wherein:
the optical resonator has an exterior surface that is functionalized to selectively bond with a target biological substance.

13. The device as in claim 3, wherein the detection unit is coupled to the laser to sweep an optical frequency of the laser probe beam over the first resonance wavelength of the TE optical mode and the second resonance wavelength of the TM optical mode to obtain spectrum of the light that is from the optical resonator and is received at the photodetector.

14. The device as in claim 13, wherein the detection unit includes a ramp signal function generator that produces a ram signal for sweeping the optical frequency of the laser probe beam.

15. The device as in claim 13, wherein the detection unit includes a lock-in amplifier that receives a detector output signal from the photodetector and processes the detector output signal with respect to a reference.

16. The device as in claim 15, wherein the detection unit operates the lock-in amplifier to produce a derivative signal from the detector output signal of the photodetector.

17. The device as in claim 13, wherein the detection unit includes a computer that receives the spectrum of the light that is from the optical resonator and is received at the photodetector.

18. A method for optically sensing a sample, comprising:
placing an optical resonator, which is structured to support transverse magnetic (TM) and transverse electric (TE) optical modes that spatially overlap, adjacent to or in contact with a sample to cause optical interaction between the sample and optical fields of light in the TM and TE optical modes;
coupling probe light into the optical resonator to cause the probe light in the TM and TE optical modes to interact with the sample; and
detecting a shift in a difference between a first resonance wavelength of a TE optical mode and a second resonance wavelength of a TM optical mode of the optical resonator to measure a change in the sample to reduce noise in the detected shift caused by thermal fluctuations in the optical resonator and the sample.

19. The method as in claim 18, comprising:
processing the detected shift in the difference between the first resonance wavelength of the TM optical mode and the second resonance wavelength of the TE optical mode to measure a change in a refractive index of the sample.

20. The method as in claim 18, comprising:
processing the detected shift in the difference between the first resonance wavelength of the TM optical mode and the second resonance wavelength of the TE optical mode to measure a change in a concentration of a chemical or biological substance in the sample.

21. The method as in claim 18, comprising:
controlling polarization of the probe light at the optical resonator to couple the probe light into the optical resonator both of the TM and TE optical modes to achieve resonances at the first resonance wavelength of the TM optical mode and at the second resonance wavelength of the TE optical mode.

22. The method as in claim 18, wherein:
the optical resonator is a whispering gallery mode resonator, and the method further includes operating an optical coupler to provide evanescent optical coupling to the whispering gallery mode resonator to couple the probe light into the whispering gallery mode resonator.

23. The method as in claim 18, wherein:
the optical resonator is a ring resonator formed by an optical waveguide, and the method further includes providing evanescent optical coupling to the optical waveguide to couple the probe light into the optical waveguide.

24. The method as in claim 18, further comprising:
sweeping an optical frequency of the laser probe beam over the first resonance wavelength of the TE optical mode and the second resonance wavelength of the TM optical mode to obtain spectrum of light that is coupled out of the optical resonator, and
using the obtained spectrum of light coupled out of the optical resonator to detect the shift in the difference between the first resonance wavelength of the TE optical mode and the second resonance wavelength of the TM optical mode of the optical resonator.

25. An optical sensing device, comprising:
an optical input module to provide laser light linearly polarized at an input polarization;
a waveguide structured to support transverse magnetic (TM) and transverse electric (TE) optical modes linearly polarized along first and second orthogonal polarizations, respectively, and located adjacent to or in contact with a sample to cause optical interaction between the sample and the light in waveguide, the waveguide placed in an optical path of the laser light from the optical input module to receive the laser light and oriented relative to the optical input module to form a 45-degree angle between and input polarization and each of the first and second orthogonal polarizations;
an output polarizer polarized at an output polarization which is at 45 degrees with respect to each of the first and second orthogonal polarizations of the waveguide and located in an optical path of light output by the waveguide to cause optical interference between a portion of light in the TE mode from the waveguide and a portion of light in the TM mode from the waveguide; and
a detection unit to receive light from the output polarizer to detect a difference between a phase shift of light in the TE mode and light in the TM mode in the output of the waveguide from the optical interference and to measure a change in the sample.

26. The device as in claim 25, comprising:
a laser that produces the laser light directed into the waveguide,
wherein the optical input module controls a polarization of the laser light from the laser to be in the input polarization.

27. A method for optically sensing a sample, comprising:
placing an optical resonator that supports two or more different optical modes relative to a sample in optical interaction between the sample and the optical resonator;
coupling probe light into the optical resonator to produce first and second different optical modes that spatially overlap with each other, the first and second optical modes having first and second optical resonances at a first resonance wavelength and a second resonance wavelength, respectively;
sweeping an optical frequency of the probe light over the first and second resonance wavelengths of the first and second optical modes;
detecting light coupled out of the optical resonator to measure a spectrum of the light coupled out of the optical resonator or waveguide based on sweeping of the optical frequency of the probe light;
using the obtained spectrum of light to obtain a difference between the first resonance wavelength of the first optical mode and the second resonance wavelength of the second optical mode; and
using the difference between the first resonance wavelength and the second resonance wavelength to determine a change in the sample while suppressing a noise caused by a temperature change.

28. The method as in claim 27, comprising:
obtaining a shift in the difference between the first resonance wavelength and the second resonance wavelength that is caused by a refractive index of the sample;
using the shift to measure a change in the refractive index of the sample.

29. The method as in claim 27, comprising:
obtaining a shift in the difference between the first resonance wavelength and the second resonance wavelength caused by a change in a concentration of a chemical or biological substance in the sample; and
using the shift to measure a change in the concentration of the chemical or biological substance in the sample.

30. The method as in claim 27, comprising:
controlling polarization of the probe light at the optical resonator to in producing the first and second different optical modes that spatially overlap with each other.

* * * * *